United States Patent [19]

Czernielewski et al.

[11] Patent Number: 5,849,776
[45] Date of Patent: Dec. 15, 1998

[54] MEDICAMENTS BASED ON METRONIDAZOLE OR ON A SYNERGIC MIXTURE OF METRONIDAZOLE AND CLINDAMYCIN

[75] Inventors: Janusz Czernielewski, Biot; Josiane Allec, Antibes; Martine Bouclier, Valbonne, all of France

[73] Assignee: Centre International de Recherches Dermatologiques Galderma (C.I.R.D. Galderma), Valbonne, France

[21] Appl. No.: 765,064

[22] PCT Filed: Jun. 20, 1995

[86] PCT No.: PCT/FR95/00819

§ 371 Date: Mar. 25, 1997

§ 102(e) Date: Mar. 25, 1997

[87] PCT Pub. No.: WO96/01117

PCT Pub. Date: Jan. 18, 1996

[30] Foreign Application Priority Data

Jul. 6, 1994 [FR] France ................... 94 08350

[51] Int. Cl.⁶ .......... A61K 31/415; A61K 31/40
[52] U.S. Cl. .......... 514/398; 514/422; 514/886; 514/887

[58] Field of Search ...................... 414/398, 422, 414/886, 887

[56] References Cited

U.S. PATENT DOCUMENTS 4,018,918   4/1977   Ayer et al. ................. 424/240

OTHER PUBLICATIONS

Chemical Abstracts AN 1993: 503333, 1993.
Chemical Abstracts AN 1976: 145357, Busch et al, 1976.
Chemical Abstracts AN 1989: 502704, Borgman et al, 1988. (Corresponds to WO 8806888, Abstract only).

*Primary Examiner*—Keith D. MacMillan
*Attorney, Agent, or Firm*—Burns, Doane, Swecker & Mathis, L.L.P.

[57] ABSTRACT

The invention relates to the use of metronidazole, or preferably of a combination of metronidazole and clindamycin, as active principle for the manufacture of pharmaceutical compositions, more particularly dermatological compositions, intended for an anti-inflammatory treatment by the topical route.

14 Claims, No Drawings

MEDICAMENTS BASED ON METRONIDAZOLE OR ON A SYNERGIC MIXTURE OF METRONIDAZOLE AND CLINDAMYCIN

The present invention generally relates to the use of metronidazole, or more preferentially still of a combination of metronidazole and clindamycin, as active principle in the manufacture of pharmaceutical compositions, more particularly dermatological compositions, intended for a curative and/or prophylactic anti-inflammatory treatment, by the topical route.

Metronidazole, or 2-methyl-5-nitroimidazole-1-ethanol, is a product which is already known per se and which is widely used for the treatment, by the topical route, of rosacea (acne rosacea) as is, for example, described in U.S. Pat. No. 4,837,378. However, the exact mechanism(s) of action by which metronidazole treats this complaint still remain unknown or purely hypothetical today, some of the explanations advanced in this respect being in fact based at the very most only on simple speculative models of in vitro type.

Conversely, it is now well established that metronidazole constitutes a particularly active antimicrobial agent which is capable of acting in the systemic treatment of certain anaerobic and parasitic infections.

Thus, there exists, to the knowledge of the Applicant company, no published data to date regarding the in vivo anti-inflammatory potential of metronidazole applied by the topical route.

Now, work carried out by the Applicant company has made it possible to demonstrate that metronidazole has a good anti-inflammatory activity after in vivo topical application.

Moreover, an absolutely outstanding synergy, at the level of this anti-inflammatory activity, has been found in the specific case where the above metronidazole is additionally combined (new combination per se, especially as a medicament) with clindamycin. The latter result is all the more unexpected and surprising since clindamycin, which is an antibiotic which is already known and commonly used in the treatment of acne by the topical route, has per se no, or substantially no, anti-inflammatory activity.

All these discoveries are the basis of the present invention.

Thus, the subject of the present invention is the use of metronidazole for the manufacture of a pharmaceutical composition intended for an anti-inflammatory treatment.

Other characteristics, aspects, objectives and advantages of the invention will become still more clearly apparent on reading the description which follows and various concrete, but in no way limiting, examples intended to illustrate it.

Preferably, the pharmaceutical composition is intended for topical use.

More particularly, the pharmaceutical composition is thus a dermatological composition.

Advantageously, use is made of a combination based on the synergic mixture of metronidazole and clindamycin for the manufacture of a pharmaceutical composition intended for an anti-inflammatory treatment.

The dermatological composition is more particularly intended for the treatment, by the topical route, of skin diseases or complaints having at least one inflammatory component or, at the same time, one inflammatory and one infectious component.

More particularly, the skin diseases or complaints correspond to skin inflammations accompanying any type of dermatoses such as eczema, psoriasis, acne rosacea, acne vulgaris, ulcers, seborrhoeic dermatitides and irritations induced by chemical, physical or mechanical agents or others.

In what follows, topical route is understood to mean any technique for administration of a product by direct application of the latter to a surface (or external) part of the body, such as the skin, and systemic route is understood to mean any technique for administration of a product by a route other than the topical route, for example the oral and/or parenteral route.

Administration of the compositions according to the invention can thus be carried out by the enteral, parenteral, topical or ocular route. However, these compositions are preferably packaged in a form suitable for an application by the topical route.

By the enteral route, the medicaments can be provided in the form of tablets, gelatin capsules, dragees, syrups, suspensions, solutions, powders, granules, emulsions or lipid or polymer vesicles or nanospheres or microspheres making possible a controlled release. By the parenteral route, the compositions can be provided in the form of solutions or suspensions for perfusion or for injection.

By the topical route, the pharmaceutical compositions based on metronidazole or on metronidazole and clindamycin, which are therefore more particularly intended for the treatment of the skin or mucous membranes, can be provided in the form of ointments, creams, milks, salves, powders, impregnated pads, solutions, gels, sprays, lotions or suspensions. They can also be provided in the form of lipid or polymer vesicles or nanospheres or microspheres or of polymer patches and of hydrogels making possible a controlled release of the active principles. These compositions by the topical route can moreover be provided either in anhydrous form or in an aqueous form, according to the clinical indication. Examples of formulations for topical use which are particularly highly suitable in the context of the implementation of the present invention are given in particular in the abovementioned U.S. Pat. No. 4,837,378, the teaching of which is, in this respect, included by way of reference in the present description.

By the ocular route, these are mainly eyewashes.

The compositions, preferably for topical use, according to the invention contain metronidazole at a concentration preferably of between 0.01% and 5% by weight with respect to the total weight of the composition and clindamycin (when it is present) at a concentration preferably of between 0.1% and 10% by weight with respect to the total weight of the composition.

According to a specific and preferred embodiment of the present invention, the overall content of the [metronidazole+clindamycin] mixture does not exceed 5 to 10% of the total weight of the medicinal compositions.

The medicinal compositions according to the invention can, of course, additionally contain inert or even pharmacodynamically or cosmetically active additives or combinations of these additives and in particular: wetting agents; depigmenting agents such as hydroquinone, azelaic acid, caffeic acid or kojic acid; emollients; hydrating agents such as glycerol, PEG 400, thiamorpholinone and its derivatives or alternatively urea; antiseborrhoeic or anti-acne agents, such as S-carboxymethylcysteine, S-benzylcysteamine, their salts or their derivatives, or benzoyl peroxide; fungicides such as ketoconazole or 4,5-polymethylene-3-isothiazolidones; carotenoids and in particular β-carotene; antipsoriatic agents such as anthralin and its derivatives; and finally 5,8,11,14-eicosatetraynoic acid and 5,8,11-eicosatriynoic acid and their esters and amides.

The compositions according to the invention can also contain flavour-improving agents, preserving agents, such as the esters of para-hydroxybenzoic acid, stabilizing agents, moisture-regulating agents, pH-regulating agents, agents for modifying osmotic pressure, emulsifying agents, UV-A and UV-B screening agents, and antioxidizing agents, such as a-tocopherol, butylated hydroxyanisole or butylated hydroxytoluene.

Of course, a person skilled in the art will take care to choose the optional compound(s) to be added to the pharmaceutical composition so that the advantageous properties intrinsically attached to the composition are not, or not substantially, detrimentally affected by the envisaged addition.

A number of examples intended, on the one hand, to demonstrate the effects attached to the present invention and, on the other hand, to illustrate various concrete formulations in accordance with the invention will now be given, without implied limitation.

EXAMPLE 1

The aim of this example is to demonstrate the in vivo topical anti-inflammatory activity of metronidazole and of a [metronidazole+clindamycin] combination.

The test used to evaluate this activity is that of oedema of the ear of the mouse induced by topical application of arachidonic acid. According to this model, the topical application of arachidonic acid to the ear causes an inflammation which is characterized by the rapid development of an oedema, the latter becoming maximum at the end of one hour after application. The oedematous response is then quantified by measuring the thickness of the ear. It should be noted that conventional non-steroidal anti-inflammatories, such as cyclooxygenase or lipoxygenase inhibitors (indomethacin, naproxen, phenylbutazone, and the like), and agents capable of blocking vascular plasma regurgitation (vasoconstrictors, and the like), are good inhibitors in this model.

The exact operating protocol is the following: the mice are first of all pretreated with the active product(s) to be evaluated, two topical applications per day (2×25 µl; one application in the morning and the other in the evening) being carried out on one of their ears of an acetone solution containing, at a given concentration, this or these active principle(s); this pretreatment is carried out for four consecutive days. Then, on the fifth day, the mice receive a last application (25 µl) of the solution containing the active principle(s) to be tested, which takes place two hours before the application to the ear thus pretreated of the arachidonic acid intended to produce the oedema (25 µl of a THF/methanol solution containing 4 weight % of arachidonic acid). The oedematous response is then quantified by measuring the thickness of the ear 1 hour and 2 hours after application of the arachidonic acid solution. The results are then expressed as % of inhibition (after 1 h and after 2 h) of the oedema with respect to the oedema observed on the other ear which had been, for its part, pretreated (under the same conditions as above) only with an acetone solution not containing active principle (control or reference ear and oedema). The results obtained are collated in the table below.

| Treatment | Doses | % Inhibition After 1 h | % Inhibition After 2 h |
|---|---|---|---|
| Metronidazole alone | 2% | 20 | 36 |
| Clindamycin alone | 2% | (ni) | (ni) |
| Metronidazole + Clindamycin | 2% + 2% | 46 | 63 |

(ni): No statistically significant inhibition

The above results clearly demonstrate, on the one hand, the good anti-inflammatory activity of metronidazole alone in the case of a treatment by the topical route and, on the other hand, the outstanding anti-inflammatory activity which is attached to the [metronidazole+clindamycin] combination in the same treatment, whereas clindamycin alone does not, by itself, have any significant activity.

EXAMPLE 2

An illustration is given here of a concrete formulation example in accordance with the invention which is provided in the form of a gel for topical use.

| | |
|---|---|
| Metronidazole | 0.75 g |
| Clindamycin phosphate | 1.18 g |
| Carbopol 980 (Goodrich) | 0.6 g |
| Polyethylene glycol 400 | 3 g |
| Sodium hydroxide q.s. | pH 5 |
| Preserving agents q.s. | |
| Demineralized water q.s. for | 100 g |

EXAMPLE 3

An illustration is given here of a concrete formulation example in accordance with the invention which is provided in the form of a cream for topical use.

| | |
|---|---|
| Metronidazole | 0.75 g |
| Methyl glucose sesquistearate | 1 g |
| Stearyl alcohol | 0.5 g |
| Liquid paraffin oil | 6 g |
| Polyethylene glycol 400 | 2 g |
| Methyl glucose sesquistearate polyoxyethylenated with 20 mol of EO | 5 g |
| Carbopol 981 (Goodrich) | 0.4 g |
| Glycerol | 7 g |
| Clindamycin phosphate | 1.18 g |
| Cyclomethicone | 4 g |
| Sodium hydroxide q.s. | pH 5 |
| Preserving agents q.s. | |
| Demineralized water q.s. for | 100 g |

We claim:

1. A method for the treatment of inflammation, said method comprising administering a composition which comprises an effective amount of metronidazole and clindamycin and a pharmaceutically acceptable carrier therefor.

2. A method for the treatment of inflammation, said method comprising topically administering a pharmaceutical composition comprising an anti-inflammatory effective amount of metronidazole and a topical pharmaceutically acceptable carrier therefor.

3. The method of claim 1, wherein the amount of metronidazole present in said composition ranges from about 0.01% to 5% by weight with respect to the total weight of the pharmaceutical composition.

4. The method of claim 2, wherein the amount of metronidazole present in said composition ranges from about 0.01% to 5% by weight with respect to the total weight of the pharmaceutical composition.

5. The method of claim 1, where said treatment of inflammation comprises treatment of a skin disease.

6. The method of claim 4, where said treatment of inflammation comprises treatment of a skin disease.

7. The method of claim 5, wherein said skin disease is accompanied by dermatosis.

8. The method of claim 6, where said skin disease is accompanied by dermatosis.

9. The method according to claim 7, wherein said dermatosis is selected from the group consisting of eczema, psoriasis, acne rosacea, acne vulgaris, ulcers, seborrhoeic dermatitides and irritations induced by chemical, physical or mechanical agents.

10. The method according to claim 8, wherein said dermatosis is selected from the group consisting of eczema, psoriasis, acne rosacea, acne vulgaris, ulcers, seborrhoeic dermatitides and irritations induced by chemical, physical or mechanical agents.

11. The method according to claim 1, wherein said clindamycin is present in said composition in a proportion ranging from 0.01% to 10% by weight with respect to the total weight of the composition.

12. The method according to claim 4, wherein said clindamycin is present in said composition in a proportion ranging from 0.01% to 10% by weight with respect to the total weight of the composition.

13. The method according to claim 1, wherein the overall content of the metronidazole and clindamycin mixture does not exceed 5 to 10% of the total weight of said composition.

14. The method according to claim 2, wherein the overall content of the metronidazole and clindamycin mixture does not exceed 5 to 10% of the total weight of said composition.

* * * * *